(12) United States Patent
Hendon et al.

(10) Patent No.: US 12,201,350 B2
(45) Date of Patent: Jan. 21, 2025

(54) REAL-TIME GUIDANCE OF RADIOFREQUENCY ABLATION CATHETER CONTACT ORIENTATION WITH CARDIAC TISSUE USING OPTICAL COHERENCE TOMOGRAPHY

(71) Applicant: THE TRUSTEES OF COLUMBIA UNIVERSITY IN THE CITY OF NEW YORK, New York, NY (US)

(72) Inventors: Christine Hendon, Bronx, NY (US); Rajinder Singh-Moon, Mastic, NY (US); Xin Yu, Guangdong (CN)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 938 days.

(21) Appl. No.: 17/215,568

(22) Filed: Mar. 29, 2021

(65) Prior Publication Data

US 2021/0307817 A1 Oct. 7, 2021

Related U.S. Application Data

(63) Continuation of application No. PCT/US2019/053817, filed on Sep. 30, 2019.
(Continued)

(51) Int. Cl.
*A61B 18/14* (2006.01)
*A61B 6/02* (2006.01)
(Continued)

(52) U.S. Cl.
CPC .......... *A61B 18/1492* (2013.01); *A61B 6/025* (2013.01); *G06N 3/045* (2023.01);
(Continued)

(58) Field of Classification Search
None
See application file for complete search history.

(56) References Cited

U.S. PATENT DOCUMENTS

2009/0088648 A1* 4/2009 Jaffe .................... A61B 5/0084
600/466
2010/0041986 A1* 2/2010 Nguyen ............... A61B 5/6852
606/33

(Continued)

OTHER PUBLICATIONS

International Search Report and Written Opinion for International Patent Application No. PCT/US2019/053817 mailed on Jan. 30, 2020.

(Continued)

*Primary Examiner* — Linda C Dvorak
*Assistant Examiner* — Nicholas S Borsch
(74) *Attorney, Agent, or Firm* — Hunton Andrews Kurth LLP

(57) ABSTRACT

An exemplary system, method and computer-accessible medium for determining particular for a portion(s) of an organ of a patient(s) can be provided, which can include, for example, receiving an in vivo optical coherence tomography (OCT) imaging information for the portion(s), and determining (i) a lesion formation on or in the portion(s), (ii) a contact of a catheter on or with the portion(s), or (iii) an angle of the catheter with respect to the portion(s), by applying a convolutional neural network(s) to the in vivo OCT imaging information.

22 Claims, 19 Drawing Sheets

Related U.S. Application Data

(60) Provisional application No. 62/739,648, filed on Oct. 1, 2018, provisional application No. 62/738,718, filed on Sep. 28, 2018.

(51) Int. Cl.
*G06N 3/045* (2023.01)
*G06T 7/00* (2017.01)

(52) U.S. Cl.
CPC .. *G06T 7/0012* (2013.01); *G06T 2207/10101* (2013.01); *G06T 2207/20081* (2013.01); *G06T 2207/20084* (2013.01); *G06T 2207/30096* (2013.01)

(56) References Cited

U.S. PATENT DOCUMENTS

| | | | |
|---|---|---|---|
| 2013/0345620 A1* | 12/2013 | Zemel | H05H 1/2418 604/24 |
| 2015/0202002 A1* | 7/2015 | Rollins | A61B 18/1492 606/41 |
| 2015/0209105 A1 | 7/2015 | Margallo Balbas et al. | |
| 2017/0265745 A1 | 9/2017 | Iddan et al. | |
| 2018/0047159 A1* | 2/2018 | Schlegl | G06N 3/04 |

OTHER PUBLICATIONS

Fleming et al. "In Vitro Characterization of Cardiac Radiofrequency Ablation Lesions Using Optical Coherence Tomography," In: Opt Express, Feb. 1, 2010.

\* cited by examiner

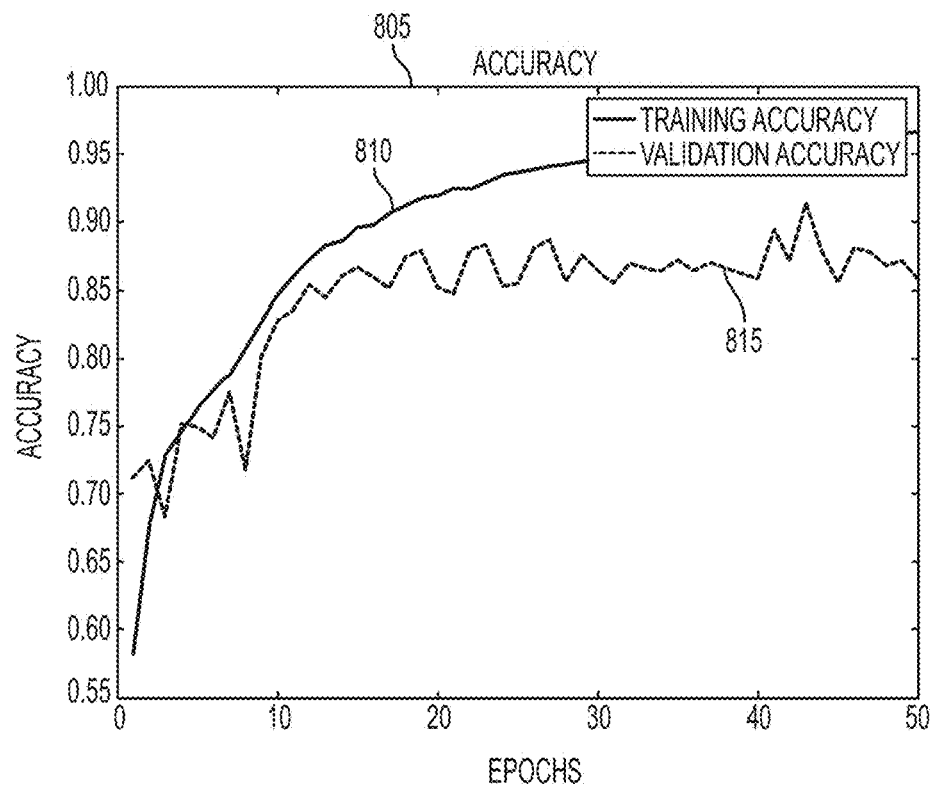
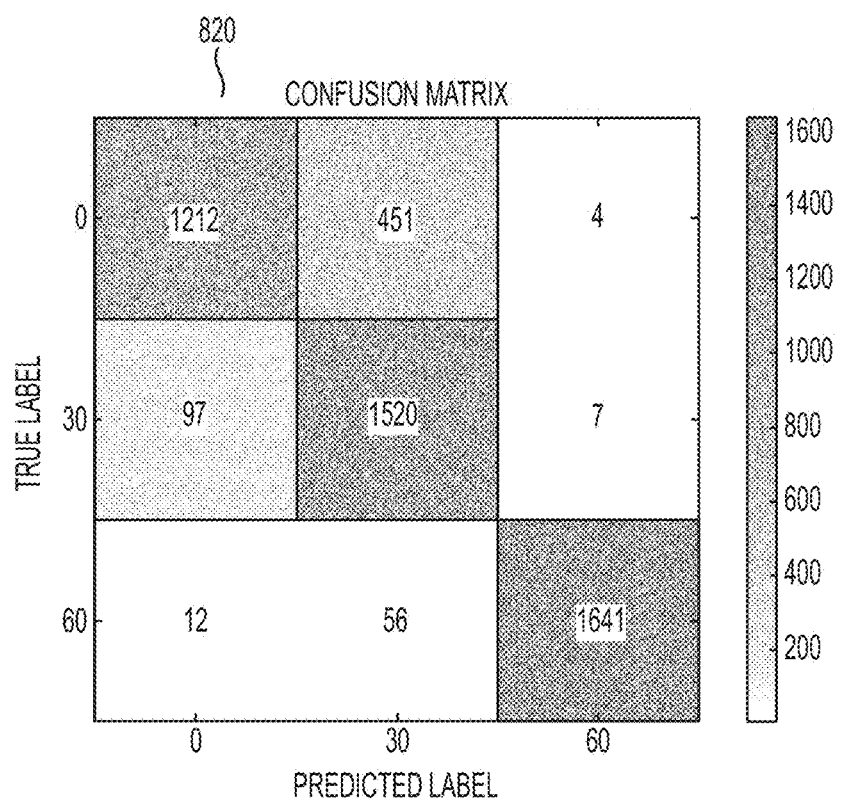
FIG. 8

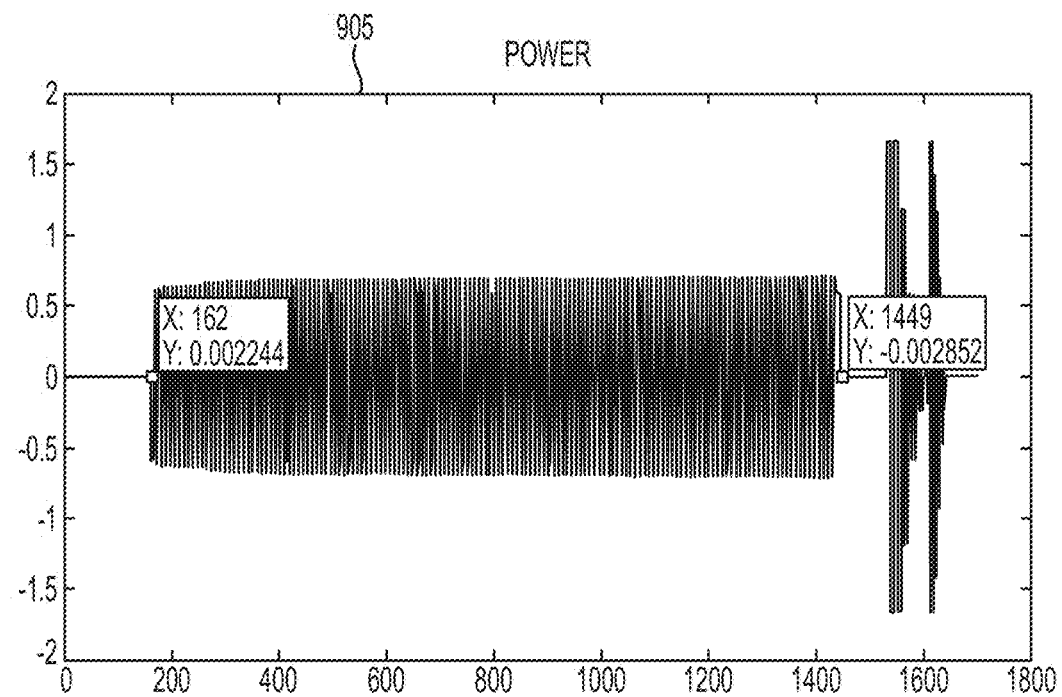
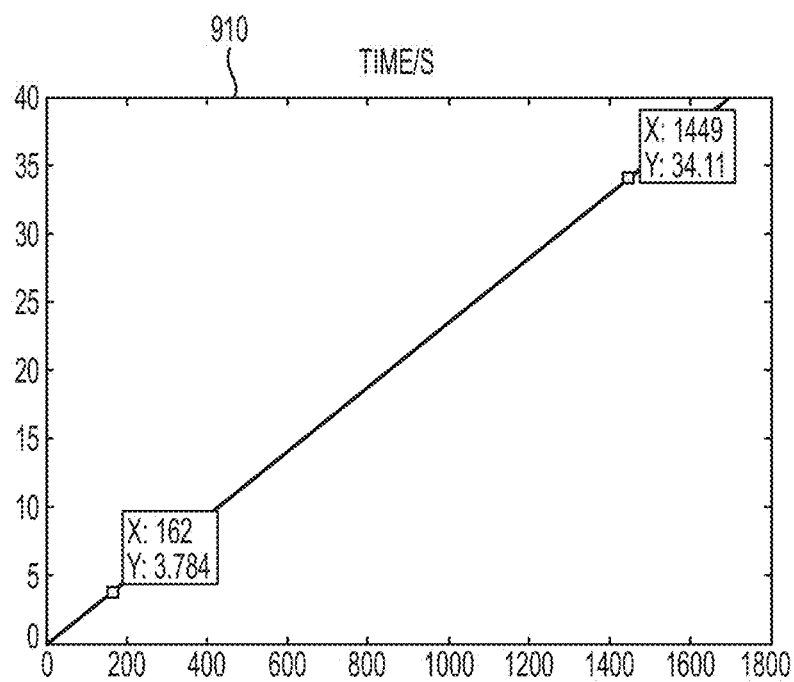
FIG. 9

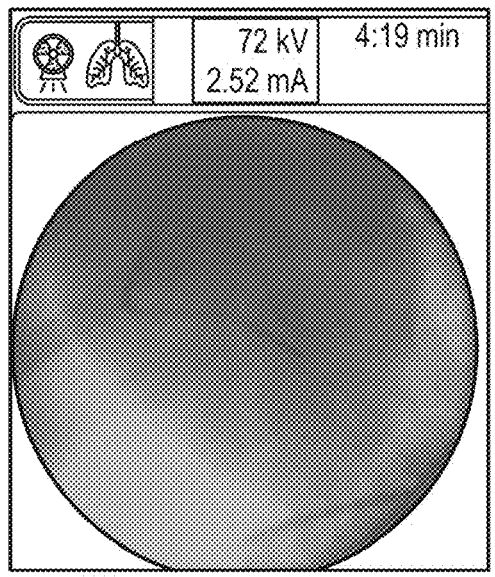
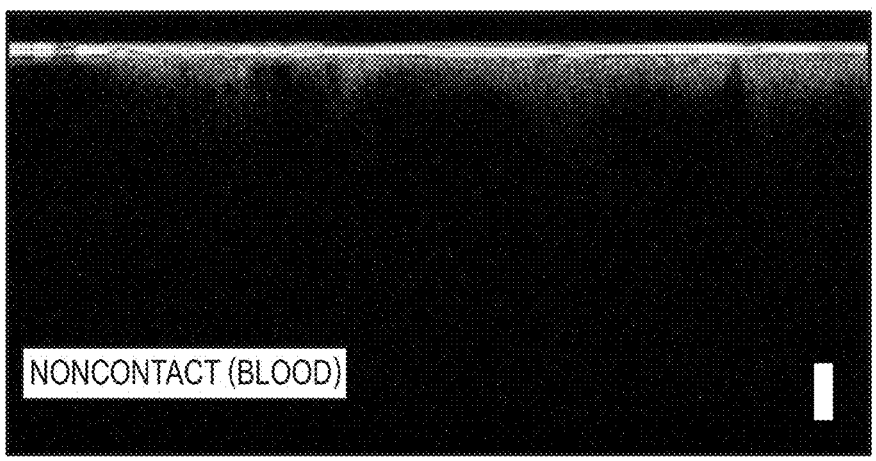
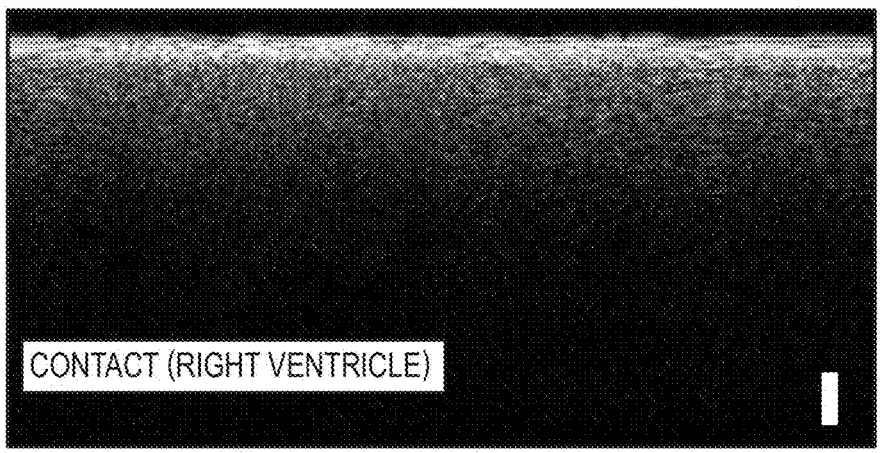
FIG. 13

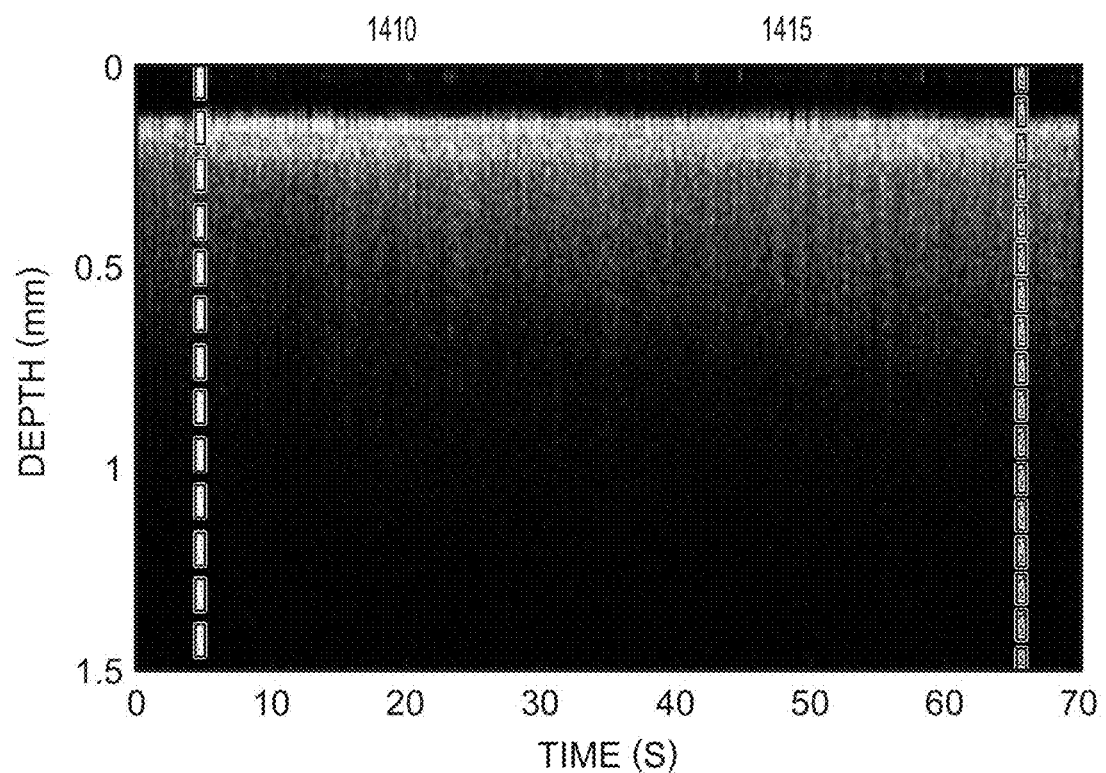
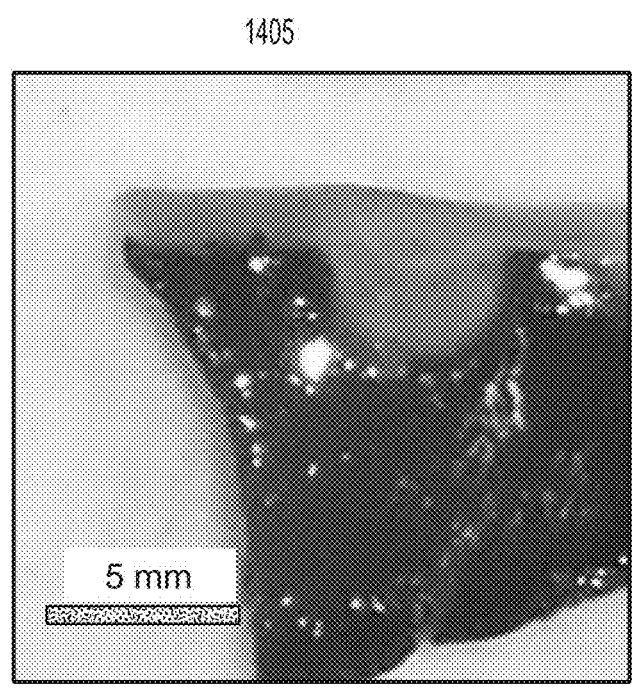
FIG. 14

1800

```
┌─────────────────────────────────────────────────────────┐
│ RECEIVING IN VIVO OPTICAL COHERENCE TOMOGRAPHY (OCT)    │─ 1805
│ IMAGING INFORMATION FOR PORTION                         │
└─────────────────────────────────────────────────────────┘
                            │
┌─────────────────────────────────────────────────────────┐
│ DETERMINE CONTACT OF CATHETER ON OR WITH PORTION BY     │─ 1810
│ APPLYING CNN                                            │
└─────────────────────────────────────────────────────────┘
                            │
┌─────────────────────────────────────────────────────────┐
│ DETERMINE ANGLE OF CATHETER ON OR WITH RESPECT TO       │─ 1815
│ PORTION BY APPLYING CNN                                 │
└─────────────────────────────────────────────────────────┘
                            │
┌─────────────────────────────────────────────────────────┐
│ CAUSE ABLATION OF PORTION                               │─ 1820
└─────────────────────────────────────────────────────────┘
                            │
┌─────────────────────────────────────────────────────────┐
│ DETERMINE LESION FORMATION ON OR IN PORTION BY          │─ 1825
│ APPLYING CNN                                            │
└─────────────────────────────────────────────────────────┘
                            │
┌─────────────────────────────────────────────────────────┐
│ CLASSIFY PORTION                                        │─ 1830
└─────────────────────────────────────────────────────────┘
```

*FIG. 18* ial Patent
REAL-TIME GUIDANCE OF RADIOFREQUENCY ABLATION CATHETER CONTACT ORIENTATION WITH CARDIAC TISSUE USING OPTICAL COHERENCE TOMOGRAPHY

CROSS-REFERENCE TO RELATED APPLICATION(S)

This application is a continuation of International Patent Application No. PCT/US2019/053817, filed on Sep. 30, 2019 that published as International Patent Publication No. WO 2020/069505 on Apr. 2, 2020, and also relates to and claims priority from U.S. Patent Application No. 62/738,718, filed on Sep. 28, 2018 and 62/739,648, filed on Oct. 1, 2018, respectively, the entire disclosures of which are incorporated herein by reference.

STATEMENT REGARDING FEDERALLY SPONSORED RESEARCH

This invention was made with government support under HL127776 awarded by the National Institutes of Health and 1454365 awarded by the National Science Foundation. The government has certain rights in the invention.

FIELD OF THE DISCLOSURE

The present disclosure relates generally to optical coherence tomography, and more specifically, to exemplary embodiments of an exemplary real-time guidance of radiofrequency ablation ("RFA") catheter contact orientation with cardiac tissue using optical coherence tomography ("OCT").

SUMMARY OF EXEMPLARY EMBODIMENTS

An exemplary system, method and computer-accessible medium for determining particular for a portion(s) of an organ of a patient(s) can be provided, which can include, for example, receiving an in vivo optical coherence tomography (OCT) imaging information for the portion(s), and determining (i) a lesion formation on or in the portion(s), (ii) a contact of a catheter on or with the portion(s), or (iii) an angle of the catheter with respect to the portion(s), by applying a convolutional neural network(s) to the in vivo OCT imaging information.

The contact of the catheter on or with the at least one portion can be determined prior to determining the angle of the catheter with respect to the portion(s) and the lesion formation on or in the portion(s). The angle of the catheter with respect to the portion(s) can be determined prior to determining the lesion formation on or in the portion(s). An ablation of the portion(s) can be caused after determining the angle of the catheter with respect to the portion(s) and prior to determining the lesion formation on or in the portion(s). An ablation of the portion(s) can be caused. The ablation can be caused using a radiofrequency ablation arrangement. The contact can be determining a contact or no contact. The angle can include (i) 0 degrees, (ii) 30 degrees, or (iii) 60 degrees.

In some exemplary embodiments of the present disclosure, the portion(s) can be classified by applying the CNN(s) to the in vivo OCT imaging information. The portion(s) can be classified as (i) treated or (ii) not treated. The CNN(s) can includes at least three CNNs, and the lesion formation on or in the one portion can be determined by applying a first CNN of the CNNs, (ii) the contact of the catheter on or with the portion(s) can be determined by applying a second CNN of the CNNs, or (iii) the angle of the catheter with respect to the portion(s) can be determined by applying a third CNN of the CNNs. The second CNN can include six layers. Three of the six layers can be consecutive rectified linear units (ReLU)-activated convolutional+Max Pooling layers. The consecutive ReLU-activated convolutional+Max Pooling layers can have a kernel size of 3×1. One of the six layers can be a ReLU-activated fully connected layer.

In some exemplary embodiments of the present disclosure, the third CNN can include at least thirteen layers. Eight of the thirteen layers can be consecutive rectified linear units (ReLU)-activated convolutional+Max Pooling layers+Average Pooling layers. Two of the thirteen layers can be ReLU-activated fully connected layers.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 8 is an exemplary graph and corresponding confusion matrix for orientation results according to an exemplary embodiment of the present disclosure;

FIG. 9 is a set of graphs illustrating catheter power and time for energy delivery according to an exemplary embodiment of the present disclosure;

FIG. 13 is an exemplary image and corresponding fluoroscopic images of a radio frequency ablation catheter being steered within a beating heart according to an exemplary embodiment of the present disclosure;

FIG. 14 is an depth chart and corresponding lesion image from m-mode optical coherence tomography imaging according to an exemplary embodiment of the present disclosure;

FIG. 18 is a flow diagram of an exemplary method for determining particular information for a portion of an organ of a patient according to an exemplary embodiment of the present disclosure.

Figure 1:
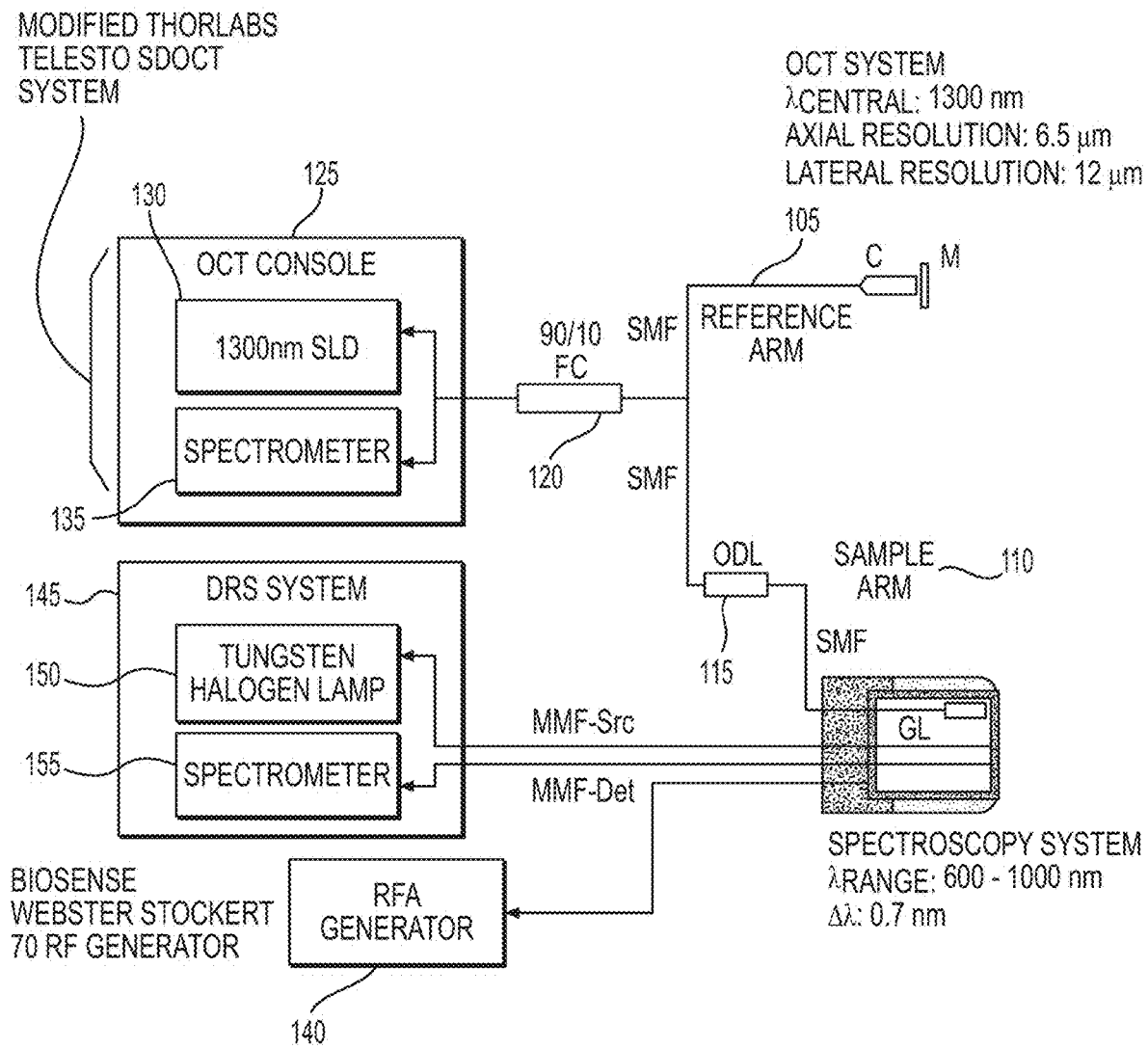
FIG. 1 is an exemplary schematic diagram of an optical coherence tomography system according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

A parameter that can affect the quality of RFA lesions that are produced is the contact angle and contact orientation. Both can be challenging to determine in vivo, and a method to classify that information and provide feedback in real time can be used to titrate the energy dose and increase the success rates of this treatment.

An exemplary optical coherence tomography ("OCT") catheter can include a grin lens-terminated single mode fiber integrated into a commercial RFA catheter to facilitate M-mode OCT imaging at the catheter tip. Atrial and ventricular wedges were dissected from four fresh swine hearts and submerged in whole blood. M-mode imaging was performed in four different orientations: (i) non-contact, (ii) 0 degrees, (iii) 30 degrees, and (iv) 60 degrees.

One exemplary contact classifier with two sub-classifiers was utilized to classify whether the catheter is in proper contact with the tissue and the angle of the catheter when it is in contact. This classifier can be based on convolutional neural networks ("CNN") and used Keras as developing framework with tensorflow backend.

A 98.51% accuracy was achieved in the "contact" or "noncontact" classifier and 91.21% in the orientation classifier with 0 degrees, 30 degrees and 60 degrees as outputs. The exemplary contact quality classifier was tested in real time and achieved high accuracy in 0.0053 seconds for 20-A-line group. These results support of having the guidance of catheter placement during the RFA therapy using OCT image and pre-trained classifiers.

FIG. 1 shows a diagram of an exemplary optical system according to an exemplary embodiment of the present disclosure. The exemplary catheter can include an integrated radiofrequency ablation probe with spectroscopy probe and OCT M-mode imaging probe. The exemplary OCT system can include a reference arm 105 and a sample arm 110, the sample arm 110 can include an optical delay line ("ODL") 115. Reference arm 105 and ODL 115 can be coupled to a fiber coupler ("FC"). FC 120 can be coupled to the exemplary OCT console 125, which can include a superluminescent diode ("SLD") 130 (e.g., a 1300 nm SLD) and a Spectrometer 135. The exemplary spectroscopy system can include a RFA generator 140. Additionally, the exemplary spectroscopy system can include a diffuse reflection spectra ("DRS") system 145, which can include a lamp 150 (e.g., a Tungsten Halogen lamp) and a spectrometer 155.

Figures 2A, 2B:
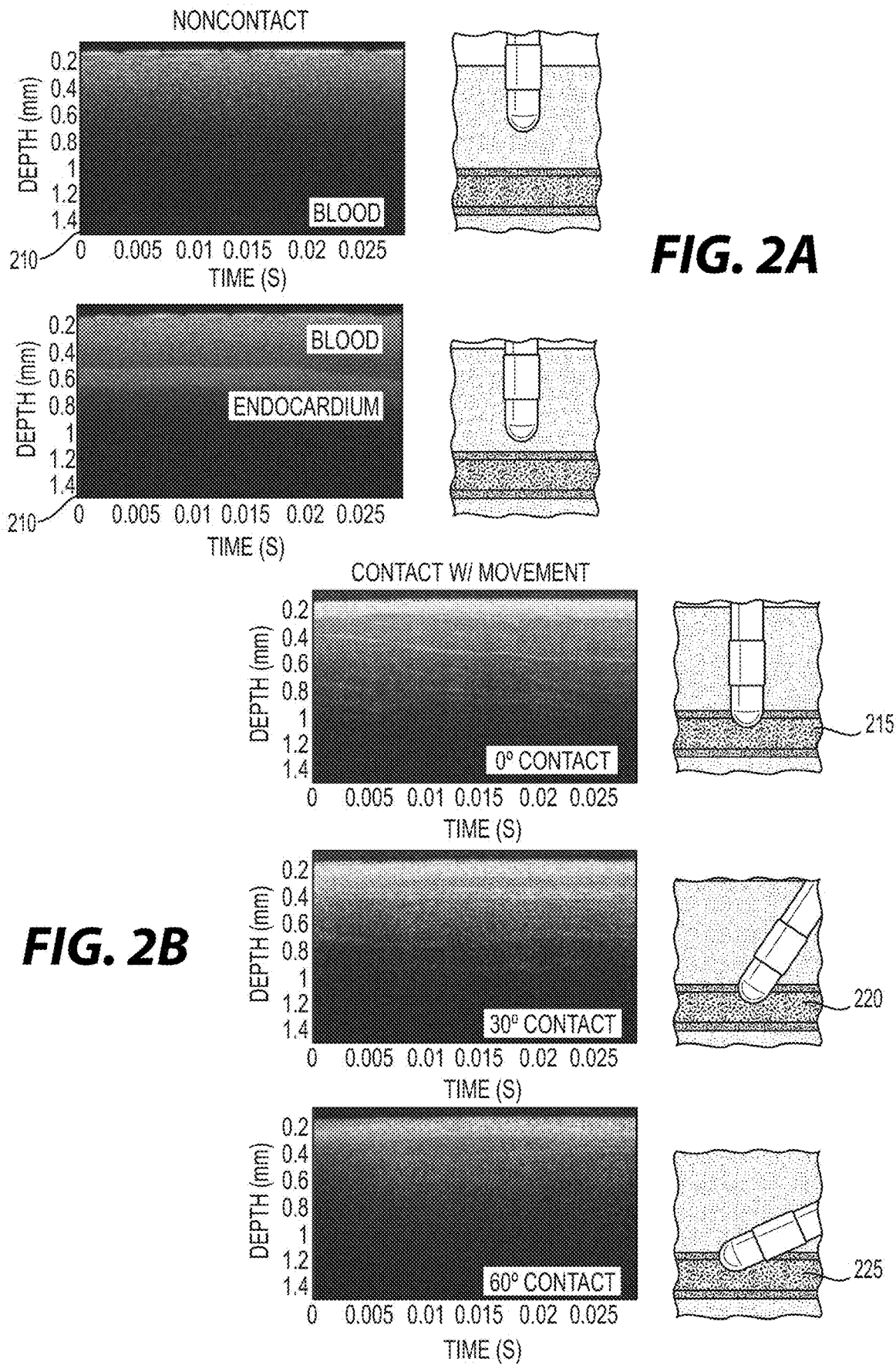
FIGS. 2A and 2B are exemplary m-mode images and corresponding catheter contact locations and angles according to an exemplary embodiment of the present disclosure.

FIGS. 2A and 2B show exemplary m-mode images and corresponding catheter contact location and angle according to an exemplary embodiment of the present disclosure. For example, FIG. 2A shows instances of the noncontact case where blood is interposed between the imaging window and the endocardium layer. FIG. 2B shows exemplary images obtained from different catheter orientations while in contact with the tissue. These data were used to develop the exemplary procedure for determining contact orientation from OCT images. Representative exemplary M-mode images were acquired during sample motion. OCT imaging can facilitate direct assessment of the tissue. When the catheter is not in contact with tissue (e.g., image 205) only blood can be observed. As the catheter begins to approach tissue (e.g., image 210), blood and the surface of the tissue can be observed. When in contact, if there is motion, tissue texture (e.g., image 215) can be readily distinguishable within M-Mode OCT images. This includes the endocardium as a highly scattering first layer, and the myocardium with visible fibers. Appreciable image penetration can be maintained even if the catheter is at an angle (e.g., images 220 and 225) with respect to the tissue surface, while the sample is submerged within blood.

Figure 3:
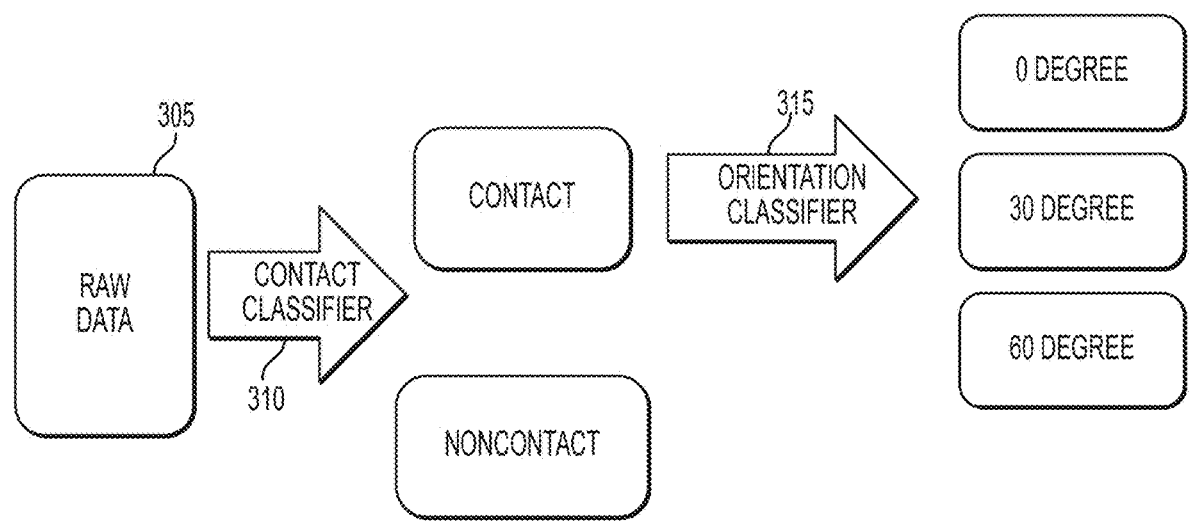
FIG. 3 is an exemplary flow diagram of a method for determining catheter contact and orientation according to an exemplary embodiment of the present disclosure.

FIG. 3 shows an exemplary flow diagram of a method for determining catheter contact and orientation according to an exemplary embodiment of the present disclosure. The input for the orientation classifier can be OCT signals. This can be a raw interferometric signal 305, A-line, or group of A-lines. The input can then be fed into a contact classifier 310 which can determine if the catheter is in contact or not in contact. If the catheter is in contact, the orientation can be determined using exemplary orientation classifier 315. As an example, orientations of 0 degree, 30 degrees, or 60 degrees can be determined, assessing how close to perpendicular the catheter is with respect to the tissue surface.

Figure 4:
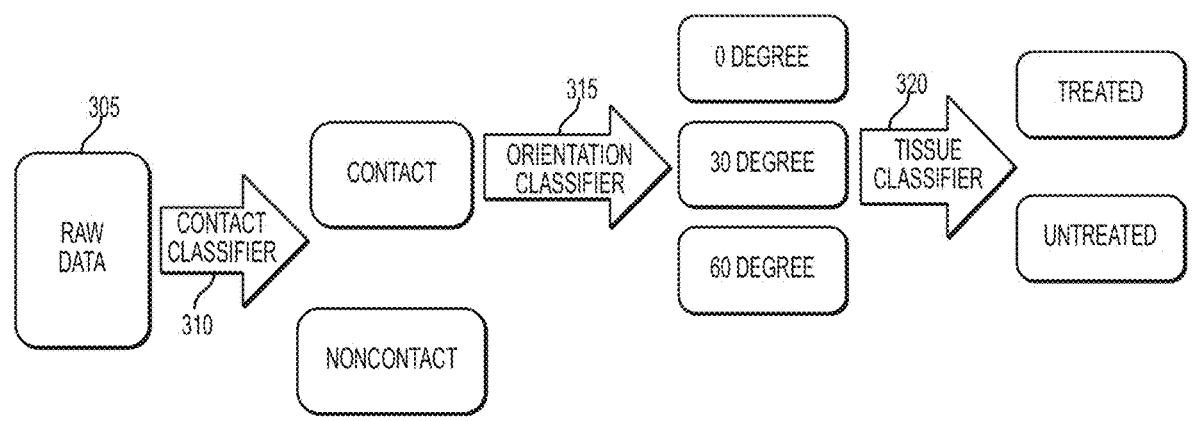
FIG. 4 is an exemplary flow diagram of a method for determining catheter contact, catheter orientation and tissue classification according to an exemplary embodiment of the present disclosure.

FIG. 4 shows an exemplary flow diagram of a method for determining catheter contact, catheter orientation and tissue classification according to an exemplary embodiment of the present disclosure. After contact and orientation can be determined as shown in FIG. 3, the OCT data can be fed into an exemplary tissue classifier 320. Exemplary tissue classifier 320 can be used to assess if the tissue can be treated (e.g., ablation lesion) or untreated (e.g., no ablation lesion). In addition, tissue composition such as fibrosis, adipose, collagen, normal myocardium, pulmonary veins can be determined based off the OCT signal.

Figure 5:
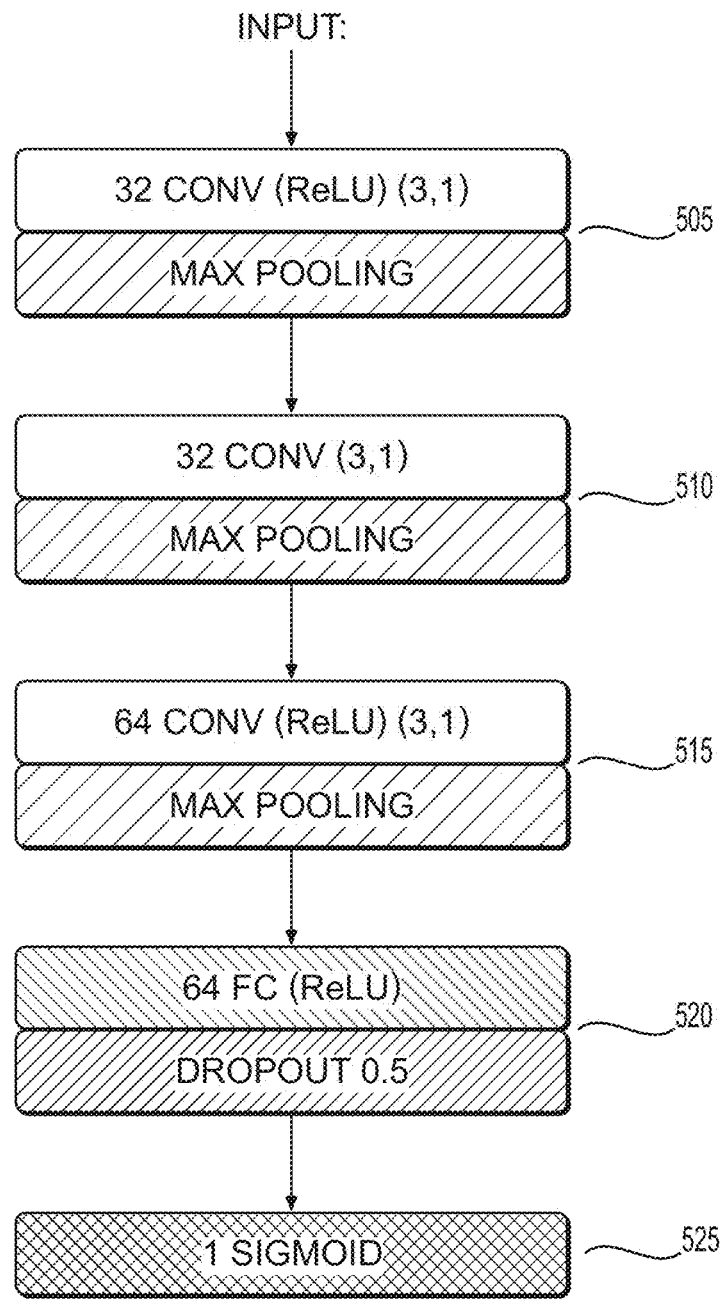
FIG. 5 is an exemplary diagram of layers of an exemplary convolutional neural network according to an exemplary embodiment of the present disclosure.

FIG. 5 shows an exemplary diagram of layers of a convolutional neural network according to an exemplary embodiment of the present disclosure. The exemplary architecture of the first stage of the contact classifier can be responsible for binary "contact" and "noncontact" discernment. The network can include 6 layers total: 1 input layer, 3 consecutive rectified linear units ("ReLU")-activated convolutional+Max Pooling layers with kernel size 3×1 (e.g., layers 505-515), 1 ReLU-activated fully connected layer 520, and 1 output layer 325. The verdict can be "contact" for output values <0.5 and "noncontact" otherwise.

Figure 6:
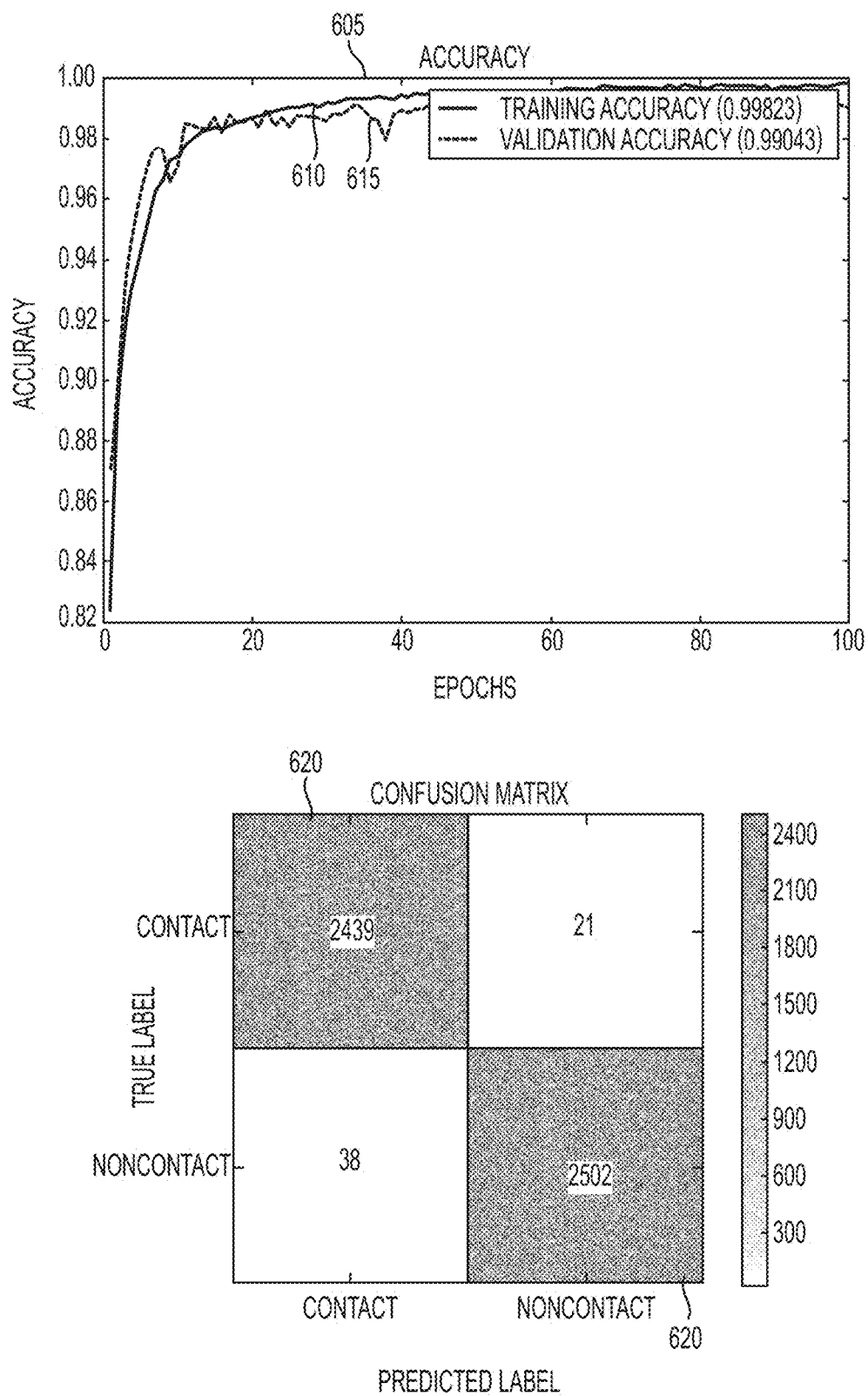
FIG. 6 is an exemplary graph and corresponding confusion matrix for classification results according to an exemplary embodiment of the present disclosure.

FIG. 6 shows an exemplary graph 605 and corresponding confusion matrix 620 for classification results according to an exemplary embodiment of the present disclosure, which illustrates exemplary results of the exemplary classifier. In particular, exemplary graph 605 illustrates training accuracy 610 and validation accuracy 615 of the contact classifier. The loss and accuracy histories are shown as a function of number of epochs for training and validation sets of the first-stage, binary contact classifier. The stochastic gradient descent was used for training, and the learning rate start from $1\;e^{-2}$ and the momentum can be 0.9. The loss function can be binary cross-entropy. Model weights converged within 100 epochs and achieved a final validation accuracy >99%. The confusion matrix of the contact classifier is shown by element 620.

Figure 7:
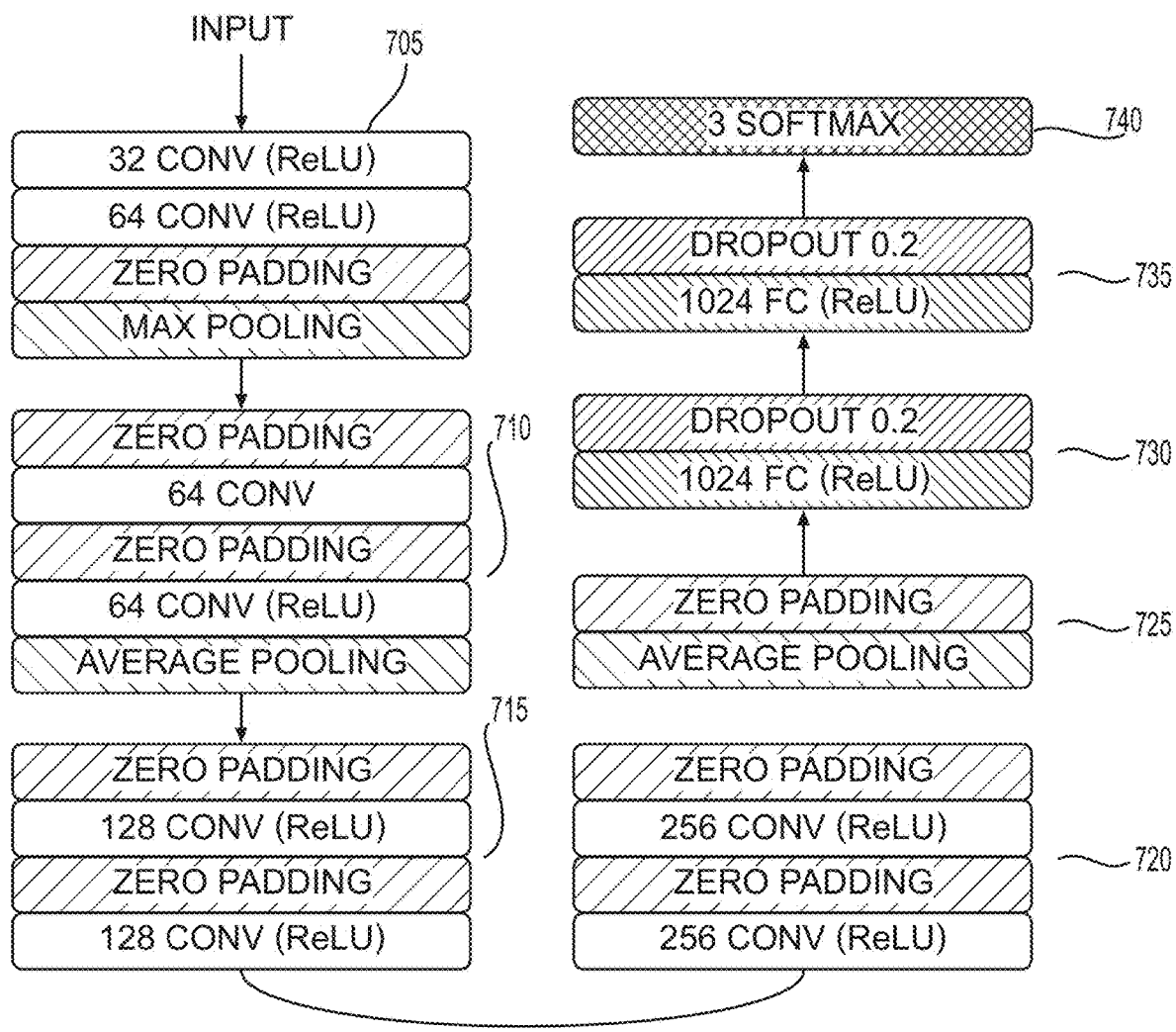
FIG. 7 is a further exemplary diagram of layers of a further exemplary convolutional neural network according to an exemplary embodiment of the present disclosure.

FIG. 7 shows a further exemplary diagram of layers of a further exemplary convolutional neural network according to an exemplary embodiment of the present disclosure. The architecture of the second stage of the contact classifier can be responsible for classifying the orientation: (i) 0 degree, (ii) 30 degree and (iii) 60 degree discernment. The exemplary network can include 13 layers total: an input layer, 8 consecutive ReLU-activated convolutional+Max Pooling layers+Average Pooling layers (e.g., layers 705-725), 2 ReLU-activated fully connected layers 730 and 735, and 1 output layer 740. The verdict can be taken to be 0 degree for output class equal to 0, 30 degree for output class equal to 1 and 60 degree otherwise. The kernel size can be (3, 3) for all the convolutional layers except for the second one.

FIG. 8 shows an exemplary graph 805 and corresponding confusion matrix 820 for orientation results according to an exemplary embodiment of the present disclosure. In particular, graph 805 illustrates the training history of the training accuracy set 810 set and validation accuracy set 815 for the orientation classifier. The adadelta was used with a default setting for training, and the learning rate start from $1e^{-1}$. The loss function can be categorical cross-entropy. It achieved 91.28% accuracy in the validation set at the end of the training.

FIG. 9 shows a set of graphs 905 and 910 illustrating catheter power and time for energy delivery according to an exemplary embodiment of the present disclosure. The catheter started to deliver the energy to the cardiac tissue at 3.78 seconds and stopped at 34 seconds.

Figure 10:
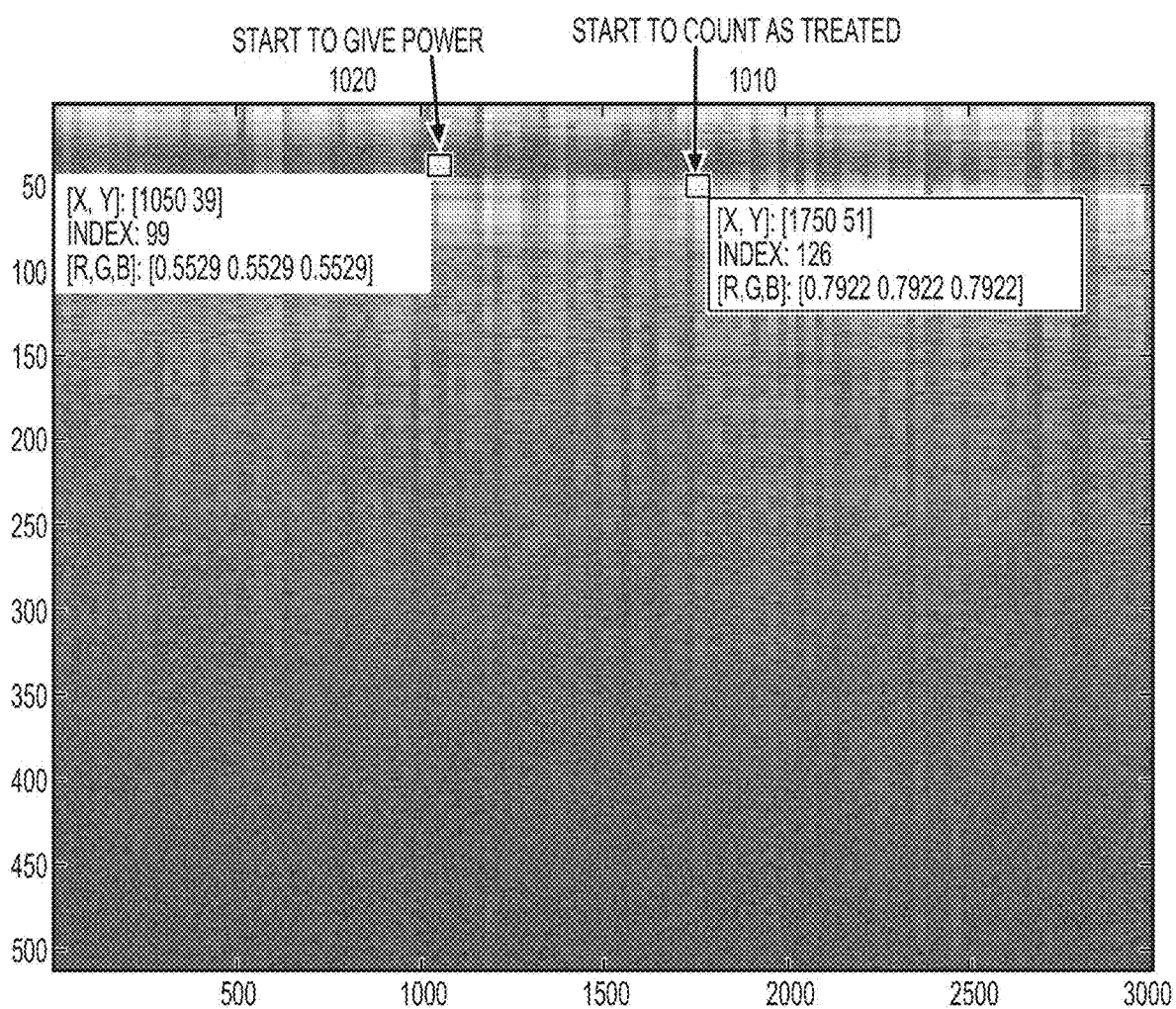
FIG. 10 is an exemplary image of a graph used to identify the time at which a lesion started to form according to an exemplary embodiment of the present disclosure.

FIG. 10 shows an exemplary image of a graph used to identify the time at which a lesion started to form according to an exemplary embodiment of the present disclosure. The exemplary Lesion classifier, can apply a decision tree with 6 nodes to identify the time in which lesions started forming (e.g., element 1010) within M-mode OCT image after power delivery commenced (e.g., element 1020).

Figure 11:
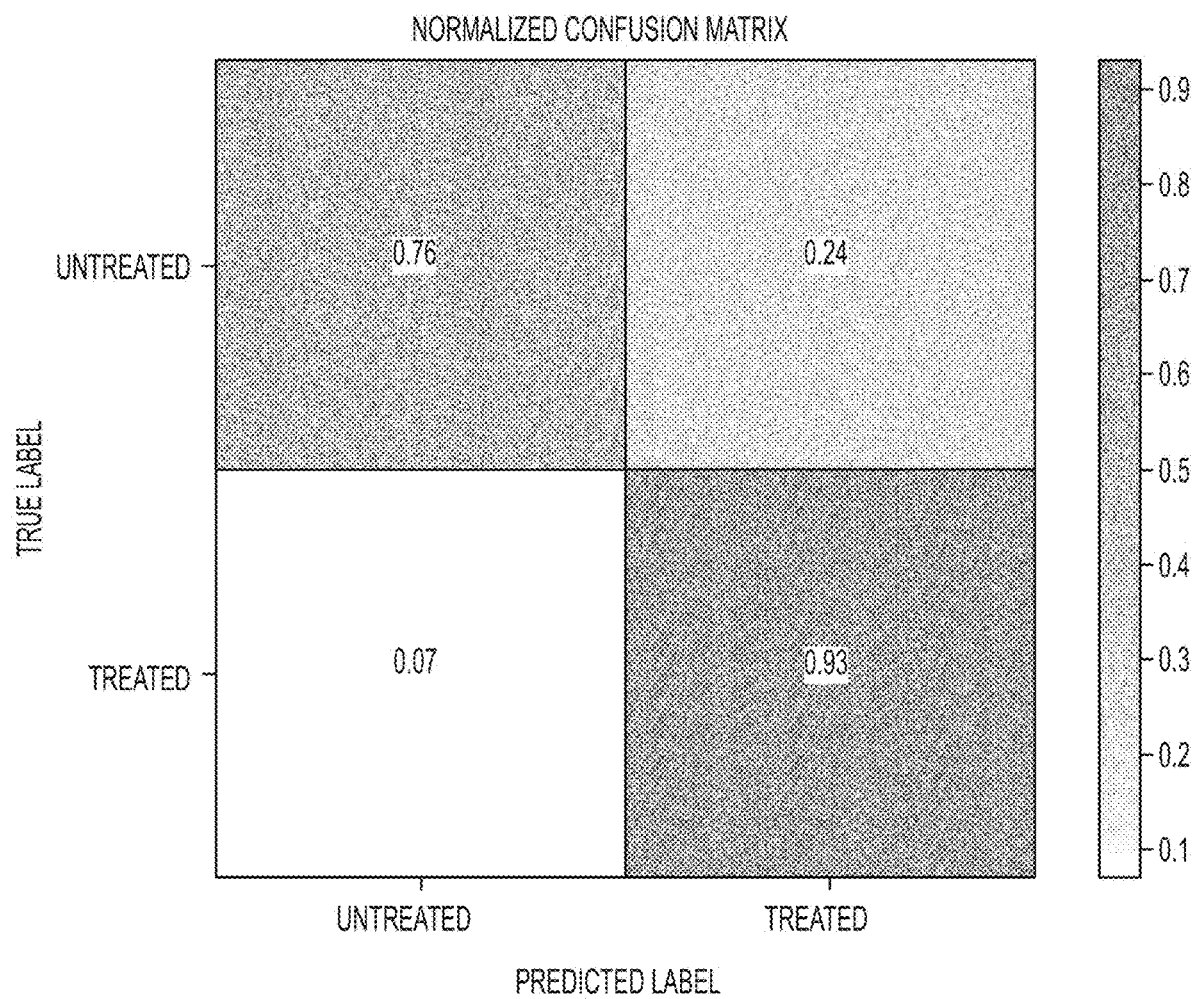
FIG. 11 is an exemplary confusion matrix for lesion classification according to an exemplary embodiment of the present disclosure.

FIG. 11 shows an exemplary confusion matrix for lesion classification according to an exemplary embodiment of the present disclosure.

Figure 12:
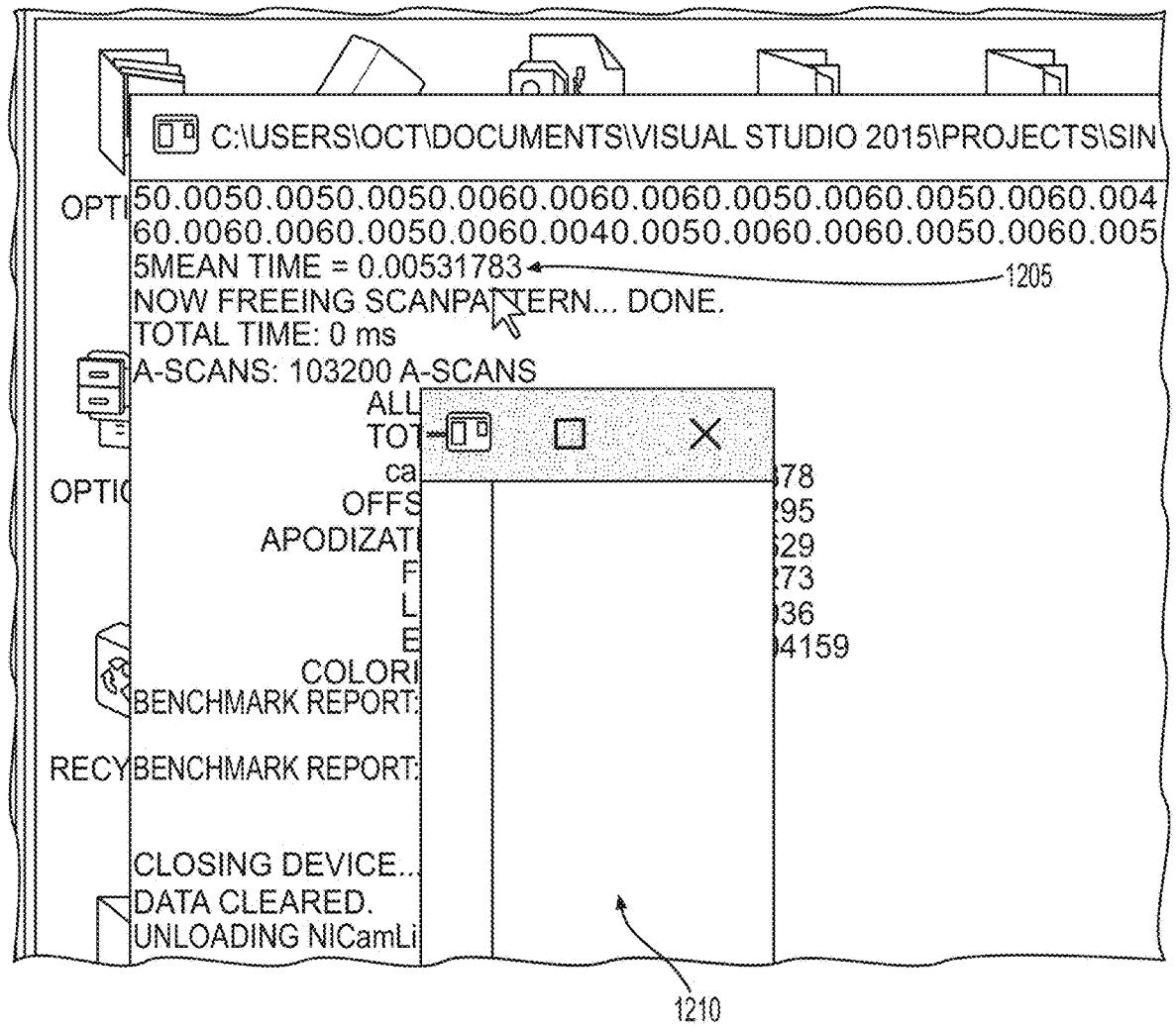
FIG. 12 is an exemplary image of the processing of A-lines in real time according to an exemplary embodiment of the present disclosure.

FIG. 12 shows an exemplary image of the processing of A-lines in real time according to an exemplary embodiment of the present disclosure. The exemplary system, method and computer-accessible medium, according to an exemplary embodiment of the present disclosure can process A-lines in real time and obtain a result within a short time, facilitating video rate processing that can provide users with direct feedback. Figure shows the exemplary network obtaining the result in 0.00531783 s (e.g., element 1205) for a group of 20 A scans (e.g., element 1210).

FIG. 13 illustrates an exemplary image and corresponding fluoroscopic images of a RFA catheter being steered within a beating heart according to an exemplary embodiment of the present disclosure. Image 1305 shows a fluoroscopic image of the optically-integrated RFA catheter being steered within the beating heart. Image 1310 shows OCT M-mode images while the catheter is floating in blood (e.g., noncontact) and when in contact with the heart wall. Established contact is confirmed by the dramatic increase in signal depth penetration (e.g., image 1315) and the absence of space between the endocardium and OCT imaging window.

FIG. 14 shows a depth chart and corresponding lesion image from m-mode OCT imaging according to an exemplary embodiment of the present disclosure. Exemplary result of M-mode OCT imaging of lesion 1405 are shown being formed in vivo between time 1410 and 1415.

Figure 15:
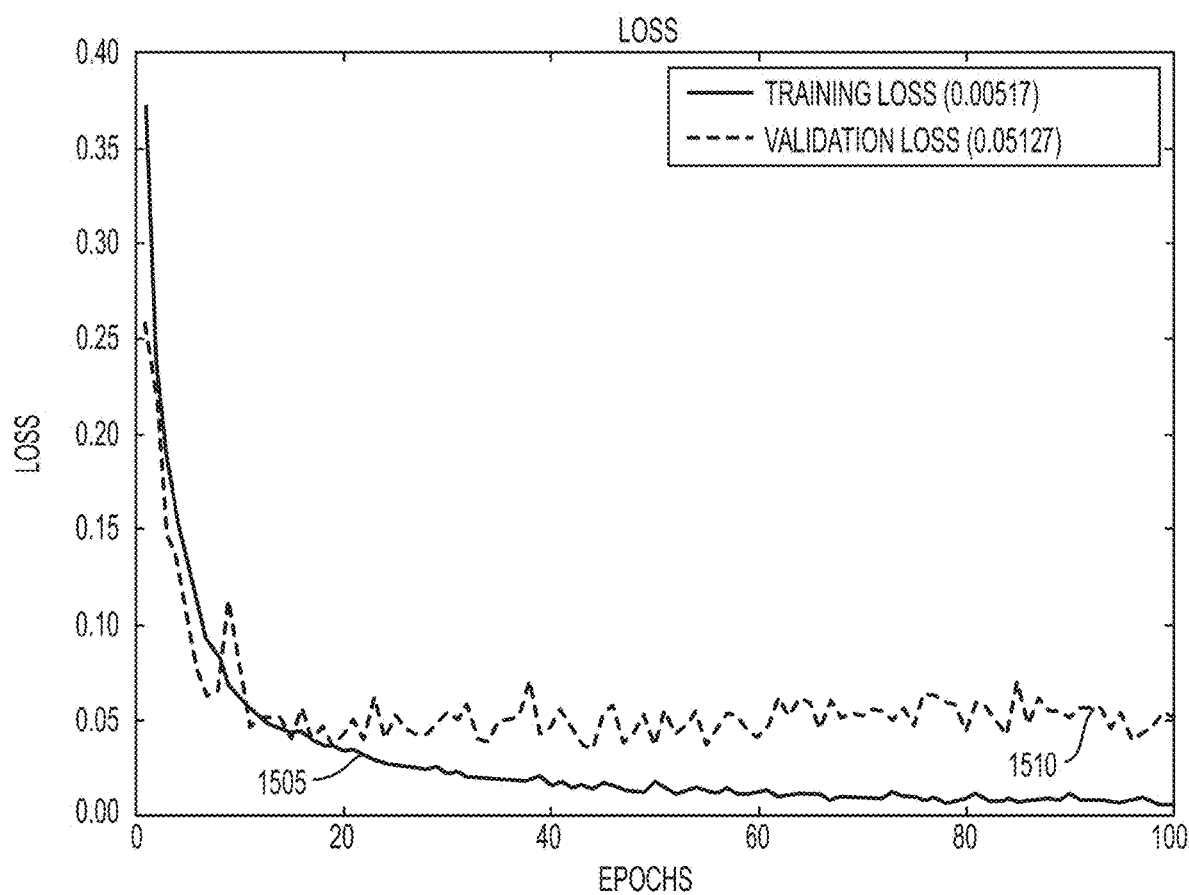
FIG. 15 is an exemplary graph illustrating accuracy history for the accuracy graphs shown in FIG. 6 according to an exemplary embodiment of the present disclosure.

FIG. 15 shows an exemplary graph illustrating accuracy history for the accuracy graphs shown in FIG. 6 according to an exemplary embodiment of the present disclosure. The training loss accuracy 1505 and validation loss accuracy 1515 are shown as a function of the number of epochs for training and validation sets of the first-stage, binary contact classifier. Model weights converged within 100 epochs and achieved a final validation accuracy >99%.

Figure 16:
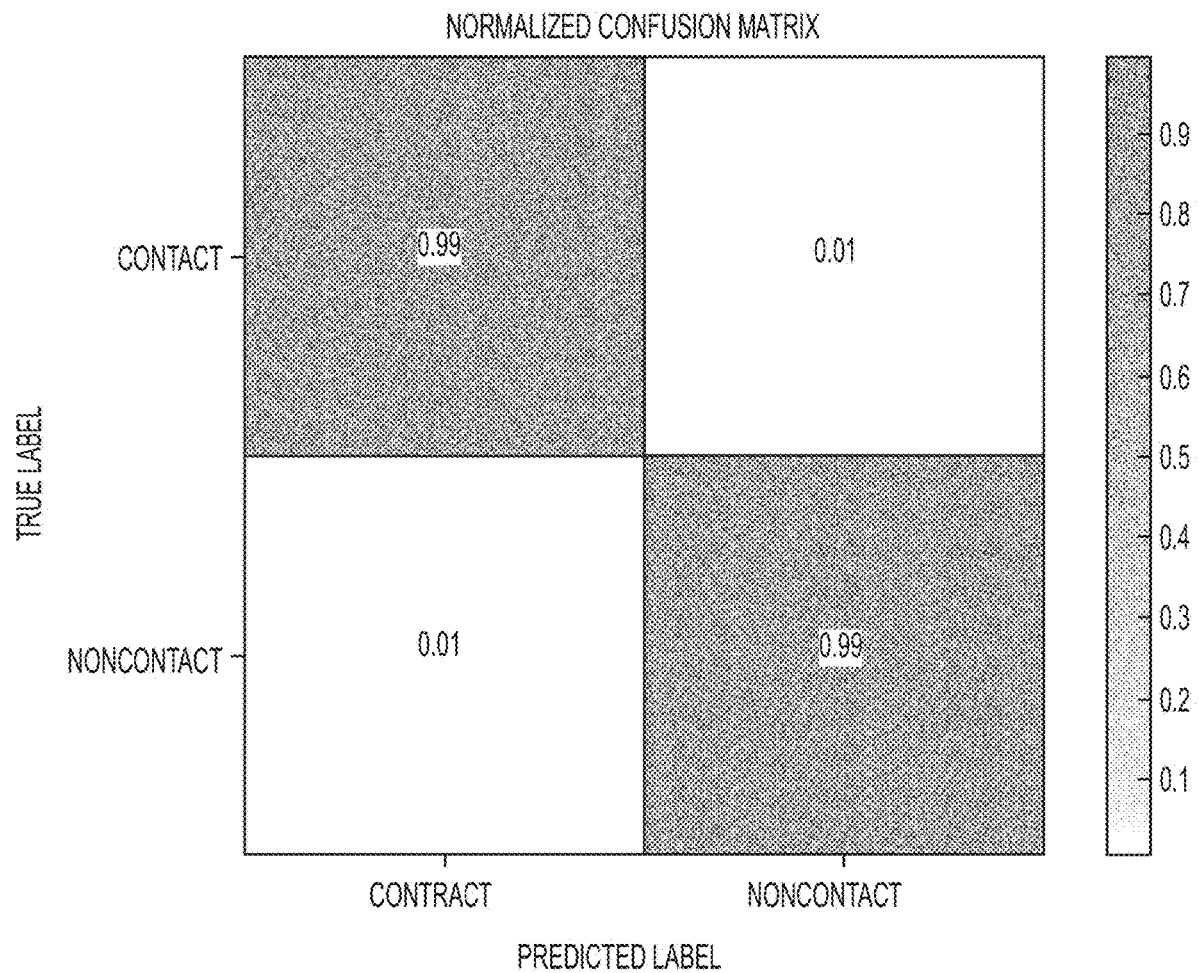
FIG. 16 is an exemplary normalized confusion matrix of the confusion matrix shown in FIG. 6 according to an exemplary embodiment of the present disclosure.

FIG. 16 shows an exemplary normalized confusion matrix of the confusion matrix shown in FIG. 6 according to an exemplary embodiment of the present disclosure. The confusion matrix is of the contact classifier. 5,000 test image were obtained to plot the confusion matrix. More than 99% of the image was classified correcting while less than 1% failed.

Figure 17:
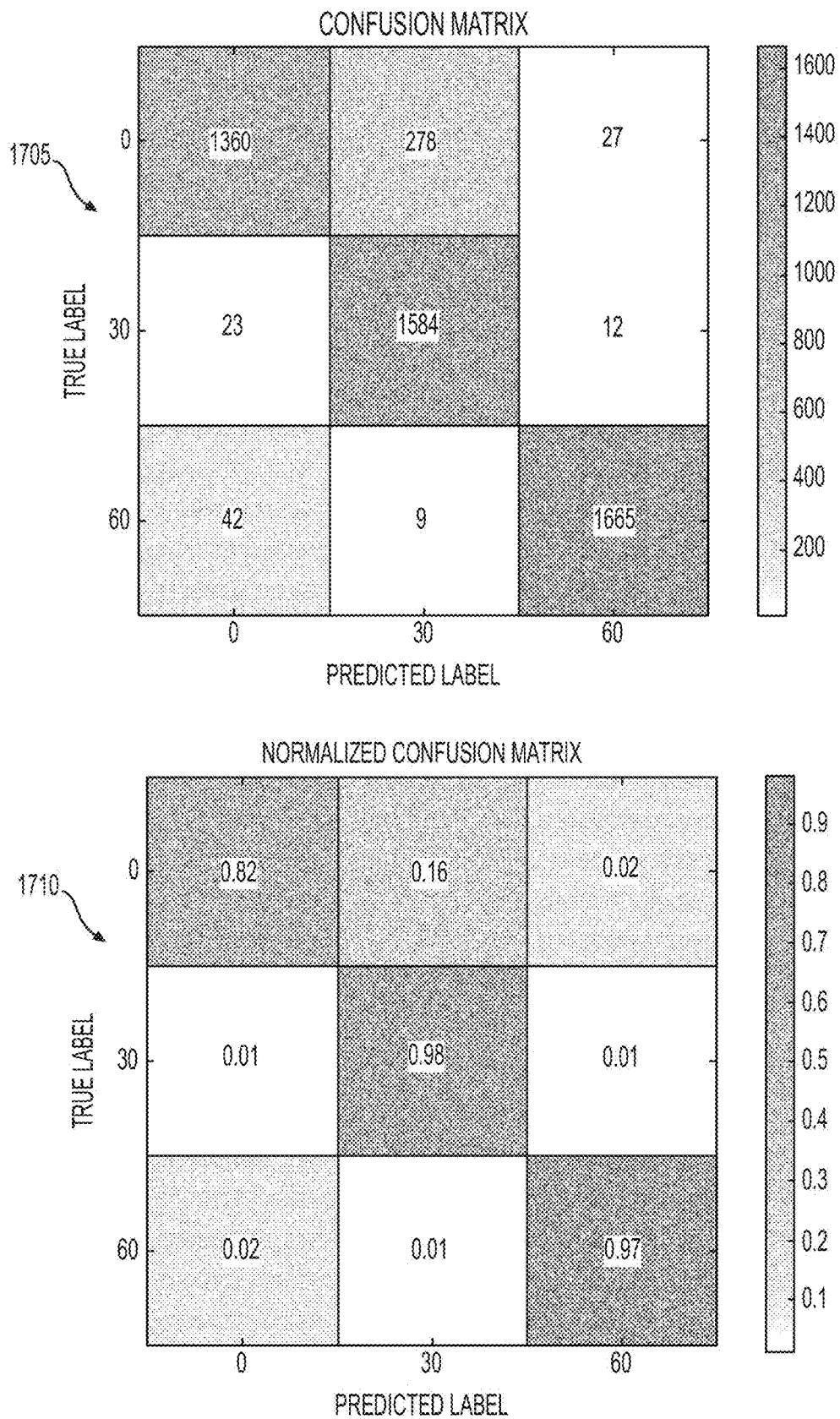
FIG. 17 is an exemplary confusion matrix and a normalized confusion matrix for the exemplary orientation classifier according to an exemplary embodiment of the present disclosure.

FIG. 17 illustrates an exemplary confusion matrix 1705 and a normalized confusion matrix 1710 for the exemplary orientation classifier according to an exemplary embodiment of the present disclosure. This can be used to illustrate that the exemplary procedure performs well in discriminating 60 degree contact from the other classes as well as 30 degree contact.

FIG. 18 shows a flow diagram of an exemplary method 1800 for determining particular information for a portion of an organ of a patient according to an exemplary embodiment of the present disclosure. For example, at procedure 1805, in vivo optical coherence tomography (OCT) imaging information for the portion of the organ can be received. At procedure 1810, a contact of a catheter on or with the portion of the organ can be determined by applying a CNN. At procedure 1815, an angle of the catheter with respect to the portion of the organ can be determined by applying a CNN. At procedure 1820, an ablation of the portion of the organ can be initiated or caused. At procedure 1825, a lesion formation on or in the portion(s) of the organ can be determined by applying a CNN. At procedure 1830, the portion of the organ can be classified.

Figure 19:
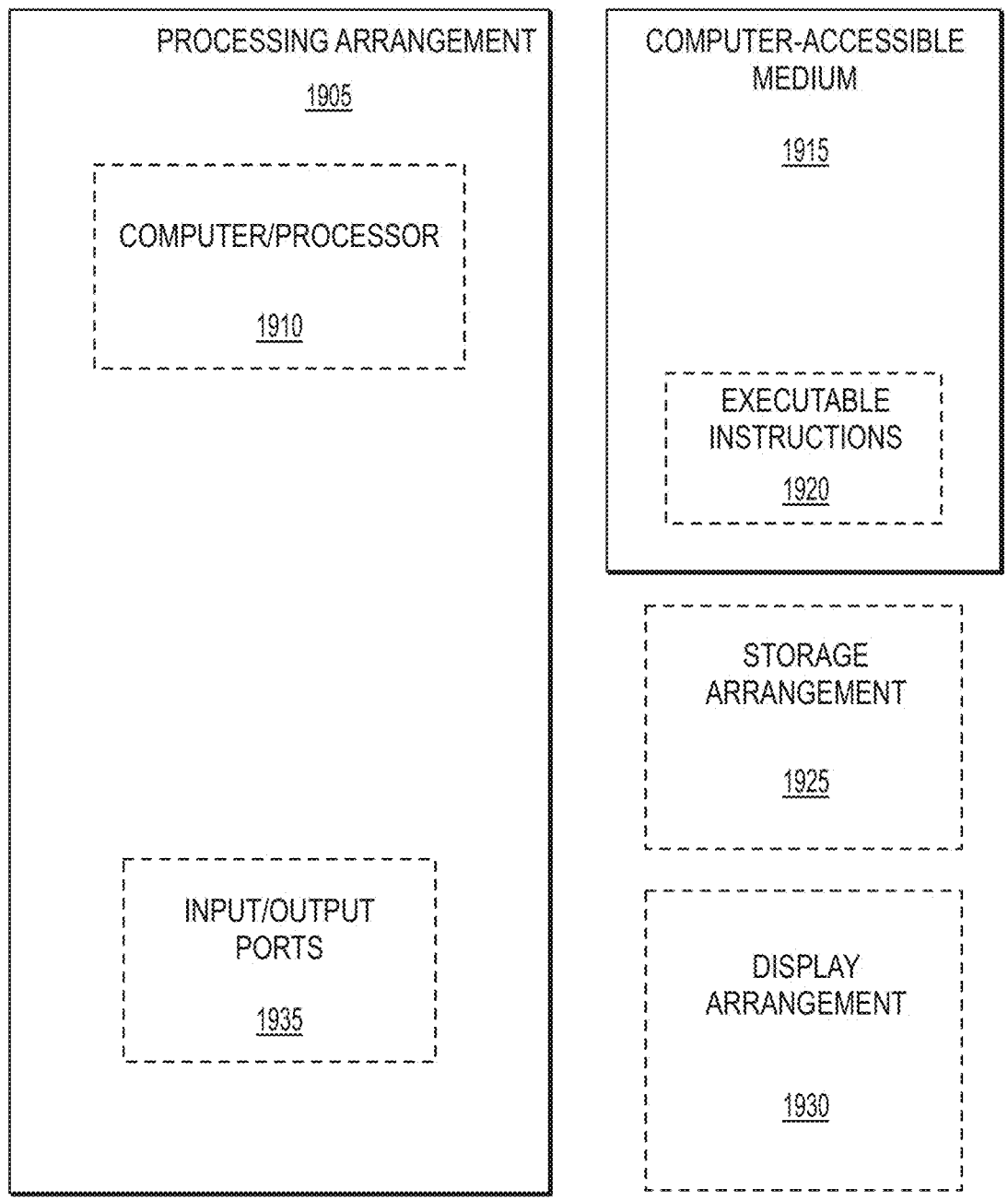
FIG. 19 is an illustration of an exemplary block diagram of an exemplary system in accordance with certain exemplary embodiments of the present disclosure.

FIG. 19 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 1905. Such processing/computing arrangement 1905 can be, for example entirely or a part of, or include, but not limited to, a computer/processor 1910 that can include, for example one or more microprocessors, and use instructions stored on a computer-accessible medium (e.g., RAM, ROM, hard drive, or other storage device).

As provided in FIG. 19, for example a computer-accessible medium 1915 (e.g., as described herein above, a storage device such as a hard disk, floppy disk, memory stick, CD-ROM, RAM, ROM, etc., or a collection thereof) can be provided (e.g., in communication with the processing arrangement 1905). The computer-accessible medium 1915 can contain executable instructions 1920 thereon. In addition or alternatively, a storage arrangement 1925 can be provided separately from the computer-accessible medium 1915, which can provide the instructions to the processing arrangement 1905 so as to configure the processing arrangement to execute certain exemplary procedures, processes, and methods, as described herein above, for example.

Further, the exemplary processing arrangement 1905 can be provided with or include an input/output ports 1935, which can include, for example a wired network, a wireless network, the internet, an intranet, a data collection probe, a sensor, etc. As shown in FIG. 19, the exemplary processing arrangement 1905 can be in communication with an exemplary display arrangement 1930, which, according to certain exemplary embodiments of the present disclosure, can be a touch-screen configured for inputting information to the processing arrangement in addition to outputting information from the processing arrangement, for example. Further, the exemplary display arrangement 1930 and/or a storage arrangement 1925 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A non-transitory computer-accessible medium having stored thereon computer-executable instructions for determining particular information for at least one portion of an organ of at least one patient, wherein, when a computer arrangement executes the instructions, the computer arrangement is configured to perform procedures comprising:
receiving an in vivo optical coherence tomography (OCT) imaging information for the at least one portion;
determining a contact of a catheter on or with the at least one portion; and
after the determination of the contact of the catheter, determining at least one of (i) a lesion formation on or in the at least one portion, or (ii) an angle of the catheter with respect to the at least one portion, by applying at least one convolutional neural network (CNN) to the in vivo OCT imaging information.

2. The computer-accessible medium of claim 1, wherein the computer arrangement is configured to determine the angle of the catheter with respect to the at least one portion prior to determining the lesion formation on or in the at least one portion.

3. The computer-accessible medium of claim 2, wherein the computer arrangement is further configured to cause an ablation of the at least one portion after determining the angle of the catheter with respect to the at least one portion and prior to determining the lesion formation on or in the at least one portion.

4. The computer-accessible medium of claim 1, wherein the computer arrangement is further configured to cause an ablation of the at least one portion.

5. The computer-accessible medium of claim 4, wherein the computer arrangement is configured to cause the ablation using a radiofrequency ablation arrangement.

6. The computer-accessible medium of claim 1, wherein the determining the contact of the catheter on or with the at least one portion includes determining a contact or no contact.

7. The computer-accessible medium of claim 1, wherein the angle includes one of (i) 0 degrees, (ii) 30 degrees, or (iii) 60 degrees.

8. The computer-accessible medium of claim 1, wherein the computer arrangement is further configured to classify the at least one portion by applying the at least one CNN to the in vivo OCT imaging information.

9. The computer-accessible medium of claim 8, wherein the computer arrangement is configured to classify the at least one portion as (i) treated or (ii) untreated.

10. The computer-accessible medium of claim 1, wherein the at least one CNN includes at least 3 CNNs, and wherein the first, second and third CNNs are different from one another.

11. A non-transitory computer-accessible medium having stored thereon computer-executable instructions for determining particular information for at least one portion of an organ of at least one patient, wherein, when a computer arrangement executes the instructions, the computer arrangement is configured to perform procedures comprising:
receiving an in vivo optical coherence tomography (OCT) imaging information for the at least one portion; and
applying at least one convolutional neural network (CNN) to the in vivo OCT imaging information determine the at least one of (i) a lesion formation on or in the at least one portion by applying a first CNN of the at least one CNN, (ii) a contact of the catheter on or with the at least one portion by applying a second CNN of the at least one CNN, or (iii) an angle of the catheter with respect to the at least one portion by applying a third CNN of the at least one CNN.

12. The computer-accessible medium of claim 11, wherein the contact of the catheter is determined by applying the second CNN that includes at least six layers.

13. The computer-accessible medium of claim 12, wherein three of the six layers are consecutive rectified linear units (ReLU)-activated convolutional+Max Pooling layers.

14. The computer-accessible medium of claim 13, wherein the consecutive ReLU-activated convolutional+Max Pooling layers have a kernel size of 3×1.

15. The computer-accessible medium of claim 14, wherein one of the six layers is a ReLU-activated fully connected layer.

16. The computer-accessible medium of claim 15, wherein eight of the at least thirteen layers are consecutive rectified linear units (ReLU)-activated convolutional+Max Pooling layers+Average Pooling layers.

17. The computer-accessible medium of claim 16, wherein two of the at least thirteen layers are ReLU-activated fully connected layers.

18. The computer-accessible medium of claim 11, wherein the third CNN includes at least thirteen layers.

19. A method for determining particular information for at least one portion of an organ of at least one patient, comprising:
receiving an in vivo optical coherence tomography (OCT) imaging information for the at least one portion;
determining a contact of a catheter on or with the at least one portion; and
after the determination of the contact of the catheter, with a computer hardware arrangement, determining at least one of (i) a lesion formation on or in the at least one portion, or (ii) an angle of the catheter with respect to the at least one portion, by applying at least one convolutional neural network to the in vivo OCT imaging information.

20. A system for determining particular information for at least one portion of an organ of at least one patient, comprising:
a computer hardware arrangement configured to:
receive an in vivo optical coherence tomography (OCT) imaging information for the at least one portion;
determining a contact of a catheter on or with the at least one portion; and
after the determination of the contact of the catheter, determine at least one of (i) a lesion formation on or in the at least one portion, or (ii) an angle of the catheter with respect to the at least one portion, by applying at least one convolutional neural network to the in vivo OCT imaging information.

21. A method for determining particular information for at least one portion of an organ of at least one patient, comprising:
receiving an in vivo optical coherence tomography (OCT) imaging information for the at least one portion; and
applying at least one convolutional neural network (CNN) to the in vivo OCT imaging information determine the at least one of (i) a lesion formation on or in the at least one portion by applying a first CNN of the at least one CNN, (ii) a contact of the catheter on or with the at least one portion by applying a second CNN of the at least one CNN, or (iii) an angle of the catheter with respect to the at least one portion by applying a third CNN of the at least one CNN.

22. A system for determining particular information for at least one portion of an organ of at least one patient, comprising:
a computer hardware arrangement configured to:
receive an in vivo optical coherence tomography (OCT) imaging information for the at least one portion; and
apply at least one convolutional neural network (CNN) to the in vivo OCT imaging information determine the at least one of (i) a lesion formation on or in the at least one portion by applying a first CNN of the at least one CNN, (ii) a contact of the catheter on or with the at least one portion by applying a second CNN of the at least one CNN, or (iii) an angle of the catheter with respect to the at least one portion by applying a third CNN of the at least one CNN.

* * * * *